(12) United States Patent
Luk et al.

(10) Patent No.: US 8,048,618 B2
(45) Date of Patent: Nov. 1, 2011

(54) METHOD FOR PREPARING AND PRESERVING A NATURAL ALLOGRAFT INTERVERTEBRAL DISK FOR HUMANS

(75) Inventors: Keith Dip Kei Luk, Pokfulam (HK); Dike Ruan, Beijing (CN)

(73) Assignee: The University of Hong Kong, Hong Kong (CN)

( * ) Notice: Subject to any disclaimer, the term of this patent is extended or adjusted under 35 U.S.C. 154(b) by 1110 days.

(21) Appl. No.: 11/768,983

(22) Filed: Jun. 27, 2007

(65) Prior Publication Data
US 2008/0027551 A1 Jan. 31, 2008

Related U.S. Application Data

(60) Provisional application No. 60/820,378, filed on Jul. 26, 2006.

(51) Int. Cl.
- *A01N 1/00* (2006.01)
- *A01N 1/02* (2006.01)
- *C12N 5/00* (2006.01)
- *C12N 5/02* (2006.01)
- *C12N 5/07* (2010.01)
- *C12N 5/10* (2006.01)

(52) U.S. Cl. .......................... 435/1.3; 435/363; 435/374

(58) Field of Classification Search .................. None
See application file for complete search history.

(56) References Cited

U.S. PATENT DOCUMENTS

| | | | |
|---|---|---|---|
| 5,108,438 A * | 4/1992 | Stone | 623/17.16 |
| 5,893,889 A | 4/1999 | Harrington | |
| 5,899,941 A | 5/1999 | Nishijima | |
| 5,928,284 A | 7/1999 | Mehdizadeh | |
| 6,080,579 A | 6/2000 | Hanley, Jr. | |
| 6,228,118 B1 | 5/2001 | Gordon | |
| 6,231,615 B1 | 5/2001 | Preissman | |
| 6,245,107 B1 | 6/2001 | Ferree | |
| 6,332,779 B1 | 12/2001 | Boyce | |
| 6,340,369 B1 | 1/2002 | Ferree | |
| 6,352,558 B1 | 3/2002 | Spector | |
| 6,454,804 B1 | 9/2002 | Ferree | |
| 6,648,919 B2 | 11/2003 | Ferree | |
| 6,682,562 B2 | 1/2004 | Viart | |
| 6,692,495 B1 | 2/2004 | Zacouto | |
| 6,706,068 B2 | 3/2004 | Ferree | |
| 6,716,245 B2 | 4/2004 | Pasquet | |
| 6,958,078 B2 | 10/2005 | Goel | |
| 6,989,032 B2 | 1/2006 | Errico | |

* cited by examiner

*Primary Examiner* — Debbie K Ware
(74) *Attorney, Agent, or Firm* — Robert D. Katz; Cooper & Dunham LLP

(57) ABSTRACT

A natural spinal disk including adjacent vertebral structures is removed from a deceased donor, rinsed in normal saline, preserved in a cryopreservative solution, and then frozen by gradually decreasing the temperature using liquid nitrogen or similar method. The implant may be thawed in normal saline solution and then implanted in a patient in need of a vertebral disk replacement.

4 Claims, 1 Drawing Sheet

METHOD FOR PREPARING AND PRESERVING A NATURAL ALLOGRAFT INTERVERTEBRAL DISK FOR HUMANS

CROSS REFERENCE TO RELATED APPLICATION

This application claims priority based on U.S. Provisional Patent Application No. 60/820,378, filed Jul. 26, 2006, the entire contents of which are incorporated herein by reference.

FIELD OF THE INVENTION

This invention relates to an intervertebral disk transplant, and to methods of preparing, preserving, and implanting such a disk transplant.

BACKGROUND OF THE INVENTION

Intervertebral disks provide mobility and a shock cushion between the vertebrae. Anatomically, a disk includes the nucleus pulposus in the center, which is composed of cells and an insoluble extracellular matrix which is produced by the nucleus itself. The extracellular matrix is composed of collagen, proteoglycans, and water. The nucleus pulposus is surrounded by the annulus fibrosis, which is also composed of cells (fibrocyte and chondrocyte), collagen fibers, and an extracellular matrix. The endplates are attached to the bony tissue, the vertebrae.

To date, there are a few treatments for degenerative disk disease. Spinal fusion has been widely used to obtain mechanical support and stability in various clinical situations, such as degenerative disk disease or infective and malignant conditions that induce spinal instability. Although results are satisfactory in most cases, long term complications, such as adjacent-segment degeneration, have been reported and remain an issue. The mechanism of this degeneration is still unclear. Cadaver studies demonstrated increasing intradisk pressures in the adjacent unfused intervertebral disks after a simulated spinal fusion. Retrospective clinical analysis suggested that the risk of adjacent-segment failure is higher for patients in whom lumbar fusion with rigid instrumentation is performed. A few studies indicate that the altered mechanical environment after short rigid spinal fusion lead to the accelerated adjacent segment degeneration.

To avoid altering the biomechanical function of the intervertebral joint, efforts have been made to develop an artificial disk, as reported a few issued patents (U.S. Pat. Nos. 6,958,078, 6,989,032, and 6,692,495 (all incorporated by reference herein)). Some of the difficulties with such developments include implant fixation, biocompatibility, and the identification of suitable materials and designs, which duplicate both form and function. Clinically, devices that replace a total disk exhibit certain weaknesses. Total disk replacements rely on attachments of the artificial disk to the vertebral endplates. Various methods of attachment have been described including the use of screws, spikes, and porous ingrowth material. The total disk/vertebral interface can loosen due to non-natural biomaterials. The problems with prosthesis loosening and revision surgery of the same are reported to be similar to that encountered with total knee and hip replacement surgery. As such, the long term outcomes of total replacement by artificial disks are still under review.

The desired treatment for degenerative disk disease therefore lies in treatment which preserves natural disk function. If disk function could be restored with biologic natural disk replacement, the weaknesses of current artificial disk replacement would be minimized, if not eliminated.

SUMMARY OF THE INVENTION

This invention provides a method for treating degenerated, diseased or traumatized human intervertebral disks of the spine. According to the method, a natural allograft disk unit is harvested from a fresh human donor. This donor disk unit preferably includes an intervertebral disk including all of its structures, including the nucleus pulposus, the annulus fibrosis, the extracellular matrix, the endplates, and a portion of the vertebrae bony tissue on either side of the disk.

The donor disk unit can be engineered and processed to alter, stimulate, remove, or insert living cells therein using methods such as temperature changes, saline or other solution washes, and shape osteotomy. The extracellular matrix and original cells may be preserved. Other related cells, for example, nucleus pulposus, annulus fibrosis cells, and stem cells are cultured and transplanted into the natural allograft disk.

The transplantation is surgically performed, and the degenerated or diseased disk is removed from the patient, including the vertebral endplates and a portion of the bony vertebra from less than 1 mm to a whole segment on either side of the disk, thereby creating a void to be filled. The natural allograft disk is positioned within the surgically created void. The invention further includes the procedures to insert, inject or surgically input one or more tissues, cells, scaffolds or substances to the natural allograft disk.

BRIEF DESCRIPTION OF THE DRAWINGS

Further features and advantages of the invention may be understood by reference to the following detailed description of the preferred embodiments, reviewed in conjunction with the following drawings in which.

DETAILED DESCRIPTION OF THE PREFERRED EMBODIMENTS

Figure 1:
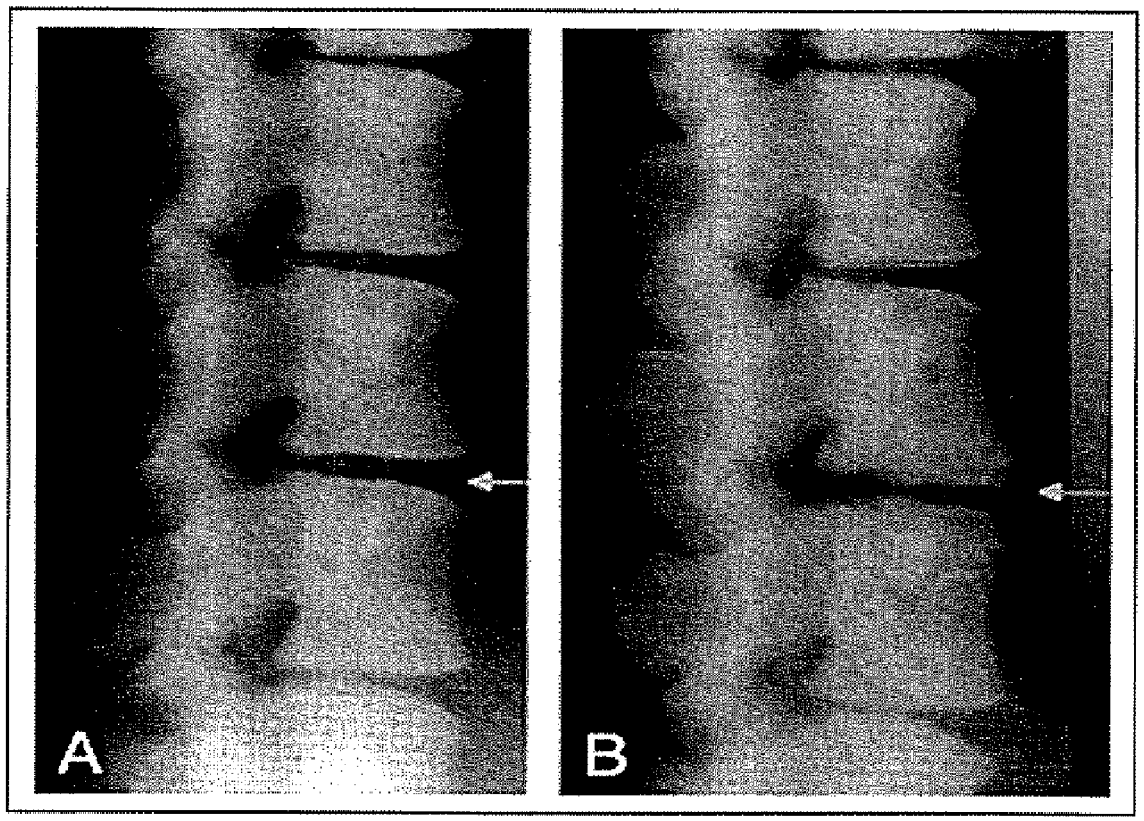
FIG. 1A is an x-ray of the spine of a patient before implantation of the allograft spinal disk of the present invention.
FIG. 1B is an x-ray of the spine of the same patient after implantation of the allograft spinal disk of the present invention.

This invention relates to a method of treating a degenerated, diseased or traumatized human intervertebral disk of the spine. According to the method, a natural allograft disk is harvested from a fresh human donor. This natural allograft preferably includes an intervertebral disk having all parts of its structure, namely the nucleus pulposus, the annulus fibrosis, the extracellular matrix, the endplates, and a portion of the vertebrae bony tissue from less than 1 mm to the whole bony vertebrae on either side of the disk. The natural allograft disk can further include growth factors, proteins, cytokines, culture media, differentiation factors, hydrogels, artificial scaffolds, antibiotics and/or useful combinations thereof. This natural allograft disk is used to restore function, and to reduce or eliminate pain in patients with degenerative or other disk disease.

Guidelines for tissue procurement including surgical technique of removal, number of hours between death of the donor and tissue procurement, and testing of the donor for infectious disease, are well described in the literature.

Preparation of the Natural Allograft Disk: The spinal column from C1 to S1 of a human donor removed up to a few hours after death is used to produce the natural allograft disk. The donor spine has to test negative for infectious diseases, as described in literature. After removal of the surrounding muscles, posterior elements, and other soft tissues, osteotomy is made at the endplates from less than 1 mm above and below the disk to including the whole vertebra. The disk grafts obtained are washed with saline solution, for example, and immersed in RPMI-1640 cryopreservative solution (10% dimethyl sulfoxide [DMSO] or similar solution) for ten minutes to 2 hours or for any longer time if needed, at 0° C. or 4° C. up to 200° C. The temperature is then reduced stepwise to 0° and then to −15° C. for 1 hour, then to −40° C. for 1 hour, or any useful combination thereof, and then −80° C. for 1 hour, after which the disk grafts are preserved in liquid nitrogen (−196° C. or lower) until surgery. The preservation period can be from one day to two years.

The natural allograft disk can be an autograft, allograft or xenograft disk comprising partially or fully decellularized annulus fibrosus, endplates and nucleus pulposus tissue of a donor vertebra. The annulus fibrosus, endplates and nucleus pulposus tissue can be cross-linked naturally or artificially. The cross-linked annulus fibrosus, endplates, and nucleus pulposus can be combined with natural or artificial scaffolds injected or surgically inserted. Preferably, the donor spinal column section is removed at the endplates approximately 0 to 60 mm above and below the donor vertebrae or disks. The disk has a predetermined 3-dimensional shape, with a width of about 5-70 mm, a depth of about 5-50 mm, and a height of about 0.5-30 mm.

After removal from the donor, the disk is washed with saline and immersed in a preservative solution such as RPMI-1640 cryopreservative solution (10% dimethyl sulfoxide [DMSO] and/or serum) for 1 minute to one month.

The temperature can also be reduced stepwise or continuously in liquid nitrogen or other liquefied gas such as helium in a laboratory freezer, or with dried ice to 0° C., then to −40° C., then to −80° C. and then finally to −200° C. where the disk is preserved in liquid nitrogen or other suitably cold fluid, or in a cryogenic freezer.

Following disk preservation, the natural allograft disk is used to replace a degenerated, diseased or traumatized human intervertebral space. Surgical techniques to remove the disk and a portion of the vertebrae are well known to spine surgeons. The natural allograft disk is either not affixed or affixed using a fixation method including suturing, tissue glue, or an adhesive bonding material to surrounding tissues of the said disk area to be treated. A resorbable or nonresorbable bone implant material can be used where deemed beneficial to help affix the disk to the adjacent bone. The natural allograft disk is then placed into the surgically created void. The surgical procedure can be as follows, for example:

With the patient under general anesthesia, the diseased intervertebral disk is exposed. After removal of the diseased disk and the adjacent bony endplates, the preserved natural allograft disk of the most compatible size is selected and quickly thawed by immersion in physiologic saline at 37° C. The disk allograft is then positioned into the slot of the excised disk without internal fixation. On recovering from anesthesia, the patient is allowed free mobilization in a few hours to a few days with or without external support.

Growth factors, such as bone morphogenic proteins, living cells and stem cells are added to the natural allograft before and/or during the surgery, and a few hours, or a few weeks, or months following the surgery. The delayed insertion of the living cells may allow revascularization of the donor bony endplates prior to cell insertion. This endplate revascularization is important for diffusion of nutrition to and from the transplanted natural allograft disk cells. Alternatively, the living cells, growth factors, or other related substances can be added to the natural allograft before, during and after surgical transplantation.

Radiological Assessment is carried out before, during and after surgical transplantation as in FIG. 1. Anteroposterior and lateral radiographs of the transplanted spine unit of the patient can be taken before surgery and immediately after the surgery, and at any period of time post surgery. The anterior, middle, and posterior disk heights are measured on the lateral radiographs using a computerized digitizer. Segmental motion can be monitored by dynamic flexion-extension radiographs. The status of hydration or degeneration of the transplanted disk can be monitored with MRI.

REFERENCES CITED

The following references are incorporated by reference herein:
U.S. Pat. No. 5,893,889
U.S. Pat. No. 5,899,941
U.S. Pat. No. 5,928,284
U.S. Pat. No. 6,080,579
U.S. Pat. No. 6,231,615
U.S. Pat. No. 6,228,118
U.S. Pat. No. 6,245,107
U.S. Pat. No. 6,332,779
U.S. Pat. No. 6,340,369
U.S. Pat. No. 6,352,558
U.S. Pat. No. 6,454,804
U.S. Pat. No. 6,648,919
U.S. Pat. No. 6,682,562
U.S. Pat. No. 6,692,495
U.S. Pat. No. 6,706,068
U.S. Pat. No. 6,716,245
U.S. Pat. No. 6,958,078
U.S. Pat. No. 6,989,032

The Invention has been described with reference to the preferred embodiments. Various modifications can be made without departing from the spirit and scope of the invention. It is therefore intended that the invention be defined by the following claims.

What is claimed is:

1. A method for preparing and preserving a natural, allograft intervertebral disk for transplantation from a human donor to a human patient, comprising:
   obtaining surgical access to an intervertebral disk in a recently deceased or soon to be deceased human donor;
   removing the intervertebral disk including at least a portion of bony vertebrae on each side thereof;
   rinsing the intervertebral disk with normal saline;
   immersing the intervertebral disk in RPM1-1640 cryopreservative solution for 10 minutes to 2 hours;
   freezing the intervertebral disk by gradually reducing the temperature thereof stepwise to about 0° C., then to about −15° C., then to about −40° C., then to about −80° C. to obtain a frozen intervertebral disk; and
   maintaining the frozen intervertebral disk at a temperature below about −150° C.

2. A method according to claim 1, wherein the intervertebral disk is preserved in liquid nitrogen for one day to two years.

3. A method according to claim 2, wherein the intervertebral disk is thawed after preservation by immersing the intervertebral disk in saline at room or body temperature.

4. A method according to claim 2, wherein the intervertebral disk is frozen in liquid nitrogen.

* * * * *